US00RE48008E

(19) United States
(12) Reissued Patent
Mossbeck

(10) Patent Number: US RE48,008 E
(45) Date of Reissued Patent: May 26, 2020

(54) ANTI-SNORE BEDDING HAVING ADJUSTABLE PORTIONS

(71) Applicant: L&P Property Management Company, South Gate, CA (US)

(72) Inventor: Niels S. Mossbeck, Carthage, MO (US)

(73) Assignee: L&P Property Management Company, South Gate, CA (US)

(21) Appl. No.: 15/213,669

(22) Filed: Jul. 19, 2016

Related U.S. Patent Documents

Reissue of:
(64) Patent No.: 7,522,062
Issued: Apr. 21, 2009
Appl. No.: 11/618,103
Filed: Dec. 29, 2006

(51) Int. Cl.
*A61G 7/043* (2006.01)
*A61G 7/015* (2006.01)
(Continued)

(52) U.S. Cl.
CPC ..... *A61G 7/018* (2013.01); *A61G 7/015* (2013.01); *A61B 7/003* (2013.01)

(58) Field of Classification Search
CPC ..... A61G 7/015; A61G 7/018; A61G 7/0573; A61B 7/003
(Continued)

(56) References Cited

U.S. PATENT DOCUMENTS 2,560,465 A 7/1951 McVicker et al.
3,013,281 A 12/1961 Steiner
(Continued)

FOREIGN PATENT DOCUMENTS

DE 1198005 8/1965
DE 1198005 B 8/1965
(Continued)

OTHER PUBLICATIONS

Decision, Institution of Inter Partes Review 37 C.F.R. § 42.108, IPR2016-00183, 28 pages.
(Continued)

*Primary Examiner* — Patricia L Engle
(74) *Attorney, Agent, or Firm* — Wood, Herron & Evans, LLP

(57) ABSTRACT

An adjustable bed includes a stationary frame, a first head deck mattress support member supported by the frame, a second seat deck mattress support member supported by the frame and pivotally coupled to the head deck mattress support member, a sensor assembly adapted to detect a sound associated with human snoring, and a motorized drive assembly operatively coupled to the sensor assembly and to the first mattress support member. The adjustable bed may be such that detection of the snoring sound actuates the motorized drive assembly thereby causing relative movement of the first mattress support member with respect to the second mattress support member. The sensor assembly may further be adapted to recognize a sound associated with snoring of a particular person and actuation of the motorized drive assembly may move the first mattress support member between an inclined position and a horizontal flat position. The sensor assembly may further be adapted, after cessation of the snoring sound for a specific length of time, to return the first mattress support member to the horizontal flat position.

20 Claims, 3 Drawing Sheets

(51) Int. Cl.
*A61G 7/018* (2006.01)
*A61B 7/00* (2006.01)

(58) Field of Classification Search
USPC ..... 5/613
See application file for complete search history.

(56) References Cited

U.S. PATENT DOCUMENTS

| | | | | |
|---|---|---|---|---|
| 3,089,130 | A | | 5/1963 | Wilson |
| 3,127,783 | A | | 4/1964 | Martens |
| 3,261,639 | A | | 7/1966 | Phillips |
| 3,317,931 | A | | 5/1967 | Benoit et al. |
| 3,644,946 | A | | 2/1972 | Swatt |
| 3,821,821 | A | | 7/1974 | Burst et al. |
| 4,385,410 | A | | 5/1983 | Elliott et al. |
| 4,559,655 | A | | 12/1985 | Peck |
| 4,788,533 | A | | 11/1988 | Mequignon |
| 4,848,360 | A | | 7/1989 | Palsgard et al. |
| 4,941,478 | A | | 7/1990 | Takeuchi et al. |
| 5,042,097 | A | | 8/1991 | Fuchs |
| 5,105,486 | A | | 4/1992 | Peterson |
| 5,165,129 | A | | 11/1992 | Rohm |
| 5,205,004 | A | | 4/1993 | Hayes et al. |
| 5,245,718 | A | | 9/1993 | Krauska |
| 5,435,317 | A | * | 7/1995 | McMahon et al. ..... 600/534 |
| 5,640,730 | A | | 6/1997 | Godette |
| 5,862,551 | A | | 1/1999 | Oguma et al. |
| 6,000,077 | A | | 12/1999 | Cyr |
| 6,061,852 | A | | 5/2000 | Bathrick et al. |
| 6,088,853 | A | | 7/2000 | Jansen |
| 6,209,157 | B1 | | 4/2001 | Hensley |
| 6,230,346 | B1 | | 5/2001 | Branson et al. |
| 6,276,011 | B1 | | 8/2001 | Antinori |
| 6,351,861 | B1 | | 3/2002 | Shows et al. |
| 6,389,622 | B1 | | 5/2002 | Her et al. |
| 6,393,641 | B1 | | 5/2002 | Hensley |
| 6,462,500 | B1 | | 10/2002 | L'Hegarat et al. |
| 6,468,234 | B1 | | 10/2002 | Van der Loos et al. |
| 6,499,162 | B1 | | 12/2002 | Lu |
| 6,640,365 | B1 | | 11/2003 | Chang |
| 6,708,358 | B2 | | 3/2004 | Hensley |
| 6,739,004 | B1 | | 5/2004 | Abrahamsen et al. |
| 6,739,005 | B2 | | 5/2004 | Davis |
| 6,754,922 | B2 | | 6/2004 | Dewert |
| 6,789,280 | B1 | | 9/2004 | Paul |
| 6,839,926 | B2 | | 1/2005 | Heimbrock et al. |
| 6,907,631 | B2 | | 6/2005 | Heaton |
| 6,951,037 | B2 | | 10/2005 | Weinman et al. |
| 6,957,460 | B2 | | 10/2005 | Horitani |
| 6,961,971 | B2 | | 11/2005 | Schneider et al. |
| 6,986,180 | B1 | | 1/2006 | Wilke |
| 6,986,182 | B2 | | 1/2006 | Mossbeck |
| 7,007,327 | B2 | | 3/2006 | Ogawa et al. |
| 7,036,165 | B2 | | 5/2006 | Weinman et al. |
| 7,093,312 | B2 | | 8/2006 | Mossbeck |
| 7,454,805 | B2 | | 11/2008 | Osborne et al. |
| 7,770,578 | B2 | | 8/2010 | Estes et al. |
| 7,992,240 | B2 | | 8/2011 | Gladney |
| 2002/0144350 | A1 | | 10/2002 | Shih |
| 2004/0194213 | A1 | | 10/2004 | Weinman et al. |
| 2004/0234080 | A1 | | 11/2004 | Hernandez et al. |
| 2005/0039263 | A1 | | 2/2005 | Reed et al. |
| 2006/0139165 | A1 | | 6/2006 | Bader |
| 2006/0162074 | A1 | | 7/2006 | Bader |
| 2010/0049073 | A1 | | 2/2010 | Bader |

FOREIGN PATENT DOCUMENTS

| | | | |
|---|---|---|---|
| DE | 4137631 | | 5/1992 |
| DE | 4137631 | A1 | 5/1992 |
| JP | 56127054 | B2 | 6/1986 |
| WO | 3603663 | A1 | 7/1986 |
| WO | WO8603663 | | 7/1986 |

OTHER PUBLICATIONS

Exhibit 1002 to Petition for IPR, U.S. Pat. No. 7,522,062 File History, 113 pages.
Exhibit 1003 to Petition for IPR, Declaration of Dr. Glen Stevick in Support of the Petition for Inter Partes Review of U.S. Patent No. 7,522,062, 131 pages.
Exhibit 1026 to Petition for IPR, Declaration of Dr. Saurabh Gupta, 2 pages.
Exhibit 1027 to Petition for IPR, Declaration of Marissa Golub, 10 pages.
Petition for Inter Partes Review of U.S. Pat. No. 7,522,062, 66 pages.
Preliminary Response by Patent Owner Pursuant to 37 C.F.R. § 42.107, 55 pages.

* cited by examiner

ANTI-SNORE BEDDING HAVING ADJUSTABLE PORTIONS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*This is a Reissue of application Ser. No. 11/618,103, filed on Dec. 29, 2006, now U.S. Pat. No. 7,522,062.*

FIELD OF THE INVENTION

The present invention relates to bedding products. More specifically, it is directed to a bed adapted to stop the snoring of a person sleeping thereon.

BACKGROUND OF THE INVENTION

Various ways have been developed to prevent snoring. Snoring may disturb persons sleeping in the same room or on the same bed as the person snoring. From time to time snoring can become so loud that it may even awaken the snoring person or others in the same room or bed. Some may deal with a snorer by waking him/her up to cause the snoring to stop, but this causes the snorer's sleep to be interrupted. Furthermore, after going back to sleep, snoring may start again, often shortly afterwards.

Snoring may occur when soft tissue in the back of a person's mouth relaxes during sleep, especially when a person sleeps on his or her back. The relaxation of the tissue may partially block the airway, which causes the body of the person to react by breathing harder, which in turn causes vibration of the tissue that results in a snoring sound. In some cases it has been determined that the snoring sounds do not occur if and as long as the person concerned sleeps in a particular position, such as lying on his or her side. Fewer people tend to snore when lying on their side, as the soft tissue may not obstruct the airway in the same manner as when the person is lying on his or her back.

Several devices have sought to address the above problem. German Patent No. 1198005, for example, teaches a device including a padded board having the same length as the upper part of a person's body and which may be hinged along the longitudinal axis of the board. The board may be equipped with a locking device that locks the part of the board that can be lifted up at an angle of between 60 degrees and 90 degrees. Such a device may be equipped at both ends with loops through which one leg and one arm are disposed so that the sleeping person is forced into the side position by the part that is lifted up. This type of device, however, may not be conducive to restful sleep since the sleeping person is pinned in a side position and is not able to turn around.

U.S. Pat. No. 3,089,130 teaches a device adapted to be mounted on a bed in which the head of the sleeping person is put on a head support that can be tilted and is equipped with a vibrator. Snoring sounds are detected by a microphone and are fed as a control signal to a control system that then activates the vibrator. By actuation of the vibrator, the head of the sleeping person is shaken up and down so that he/she wakes up, thereby causing the snoring to cease. Such a device also has the disadvantage of interrupting the sleep of the person, often numerous times throughout the night.

U.S. Pat. No. 4,788,533 teaches a device for interrupting the snoring of a sleeping person as soon as the snoring begins. The device includes a microphone which picks up the snoring noise emitted by an individual and compares the intensity of the snoring noise detected by the microphone to a threshold level. In the event the detected noise is above the threshold, a sound device is actuated which does not awaken the subject but does subconsciously cause a change in behavior in the subject.

U.S. Pat. No. 4,848,360 discloses a device for preventing the snoring of a sleeping person which again does not wake the person. The device includes a box having a microphone which picks up the snoring noise emitted by an individual and filters out other sounds. In the event the snoring continues for more than a specified period of time, i.e. thirty seconds, a vibrator is actuated which does not awaken the subject but does influence him/her to change his or her sleeping position.

The use of these devices does not provide that the snorer will change his or her sleeping position to stop the snoring without waking the snorer. Therefore there is a need for a bedding product and associated method suitable to stop a person's snoring by changing his or her sleeping position without substantially disturbing his/her sleep.

SUMMARY OF THE INVENTION

These and other problems in the prior art are addressed by this invention which, in one embodiment, includes an adjustable bed having a stationary frame, a first head deck mattress support member supported by the frame, a second seat deck mattress support member supported by the frame and pivotally coupled to the head deck mattress member, a sensor assembly adapted to detect a sound associated with human snoring, and a motorized drive assembly operatively coupled to the sensor assembly and to the first mattress member. The adjustable bed may be such that detection of the snoring sound actuates the motorized drive assembly thereby causing relative movement of the first mattress member with respect to the second mattress member.

The sensor assembly may further be adapted to recognize a sound associated with snoring of a particular person and actuation of the motorized drive assembly may move the first mattress member between an inclined position and a horizontal flat position.

In one aspect of the invention, an adjustable bed may include a first mattress member having a first edge, a second mattress member having a second edge generally parallel to and adjacent the first edge, and a pivotal coupling of the first and second mattress members along the first edge. In another aspect of the invention, the relative movement of the first mattress member with respect to the second mattress member may include incremental relative movements.

In another embodiment, an adjustable bed may include a stationary frame, a first head deck mattress support member supported by the frame, at least one other mattress support member supported by the frame being pivotally coupled to the first mattress support member, a sensor assembly adapted to detect a sound associated with human snoring, and a motorized drive assembly operatively coupled to the sensor assembly and to the first mattress support member. The adjustable bed may be such that detection of the snoring sound actuates the motorized drive assembly thereby causing relative movement of the first mattress support member with respect to the at least one other mattress support member.

The adjustable bed in this embodiment may be such that the first mattress support member includes a first edge, one of the other mattress support members includes a second edge generally parallel to and adjacent the first edge, and such that the first mattress support member and one other mattress support member are pivotally coupled along the first edge.

Advantageously, the embodiments herein described provide an adjustable bed suitable to stop a person's snoring by changing the relative positions of one or more mattress members thereby causing cessation of the snoring without disturbing the sleep of the person sleeping on the bed.

BRIEF DESCRIPTION OF THE DRAWINGS

These and other objectives and advantages will become readily apparent to those of ordinary skill in the art from the following description of embodiments of the invention and from the drawings in which.

DETAILED DESCRIPTION

Figure 1:
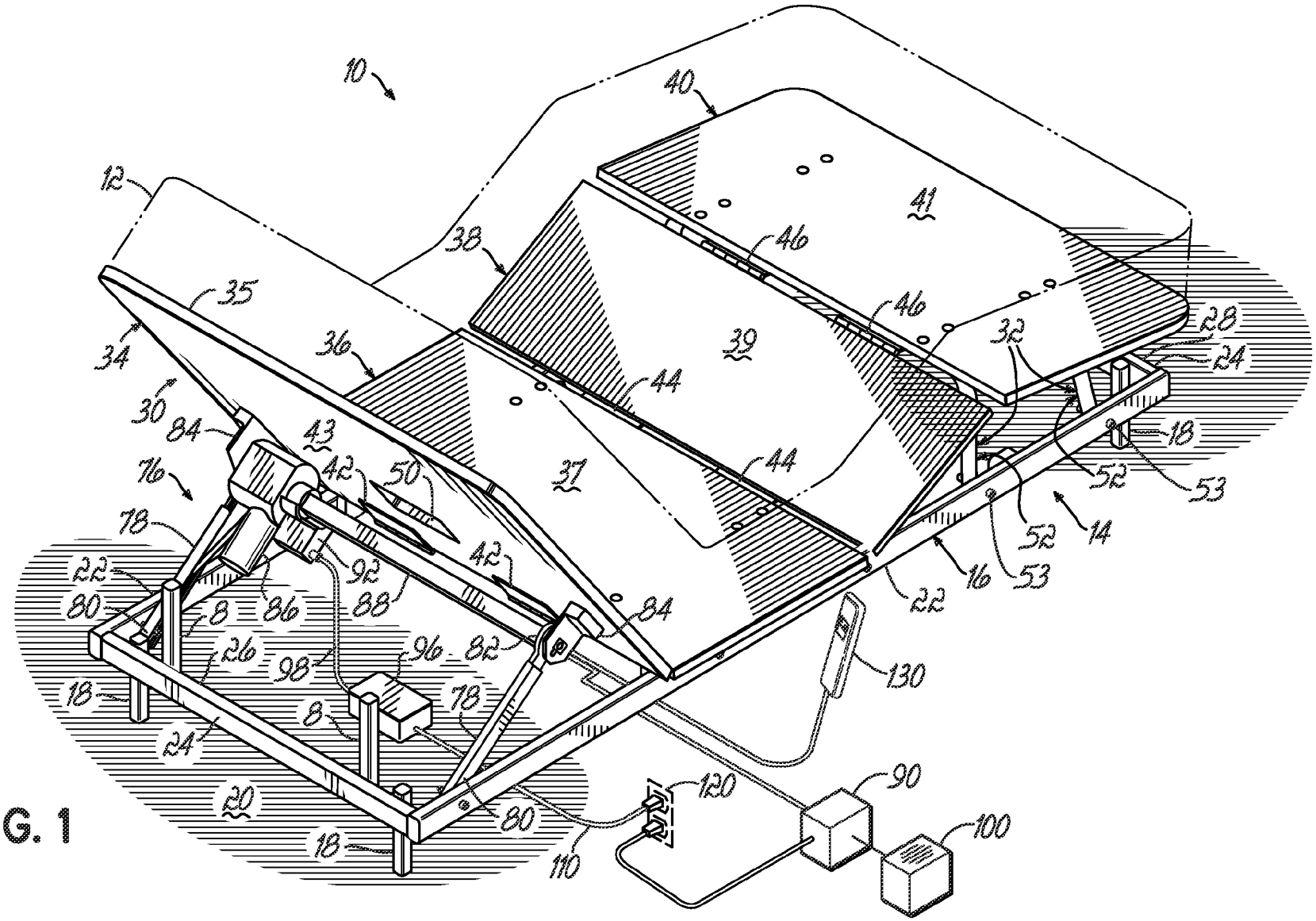
FIG. 1 is a perspective view of an adjustable bed made in accordance with the principles of this invention in a fully inclined position supporting a mattress shown in phantom.
Figure 2:
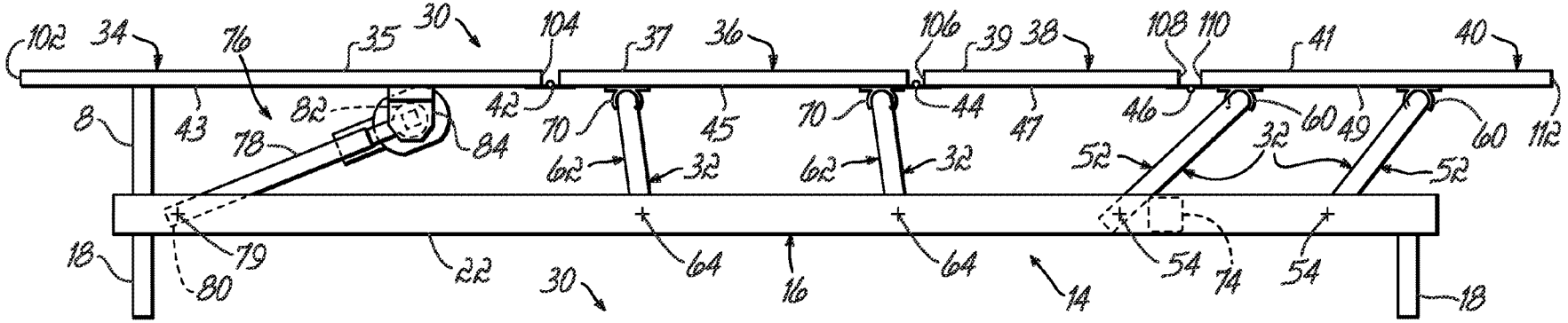
FIG. 2 is a side elevational view of the adjustable bed of FIG. 1 without the mattress and in a fully horizontal position.

Referring to the drawings, particularly to FIGS. 1-2, an exemplary bedding product in the form of an adjustable bed 10 includes a mattress 12 that can be of any conventional type such as an air mattress, a coil spring mattress or any other type of mattress. Similarly, the adjustable bed 10 may be any conventional adjustable bed, such as that described in U.S. Pat. No. 7,093,312, the disclosure of which is herein incorporated by reference in its entirety.

With reference to FIG. 2, the adjustable bed 10 is movable between a fully horizontal position and a fully inclined position (FIG. 1). An operator or user may sleep with the adjustable bed 10 generally in its fully horizontal position, in the fully inclined position, or in any position therebetween.

The adjustable bed 10 may comprise a base 14 including a generally rectangular stationary frame 16 and four legs 18 supporting the frame 16 a fixed distance about a floor or supporting surface 20. The stationary frame 16 comprises a pair of opposed side rails 22 and a pair of opposed end rails 24 extending between the side rails 22 at the ends thereof. The end rails 24 include a head rail 26 and a foot rail 28. The legs 18 may be secured to the end rails 24 or may alternatively be secured to the side rails 22.

Figure 3:
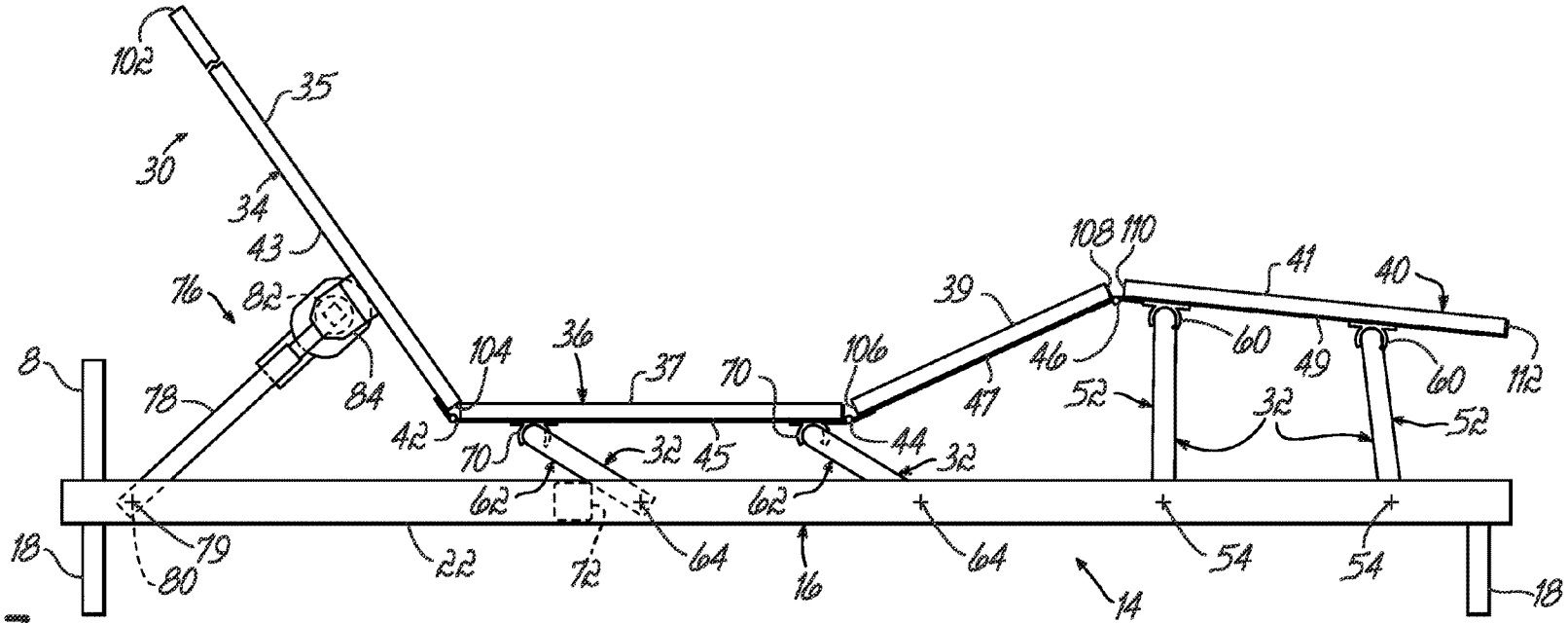
FIG. 3 is a side elevational view of the adjustable bed of FIG. 1 without the mattress and in a fully inclined position.

With reference to FIGS. 2-3, an articulated deck 30 is spaced above the stationary frame 16 with a plurality of connectors 32. The articulated deck 30 comprises a head deck board 34, a seat deck board 36, a leg deck board 38 and a foot deck board 40. The deck boards may be of equal width but any two deck boards may alternatively be of different widths. Deck boards 34, 36, 38 and 40 have upper surfaces 35, 37, 39 and 41, respectively, and lower surfaces 43, 45, 47 and 49, respectively.

Figure 4:
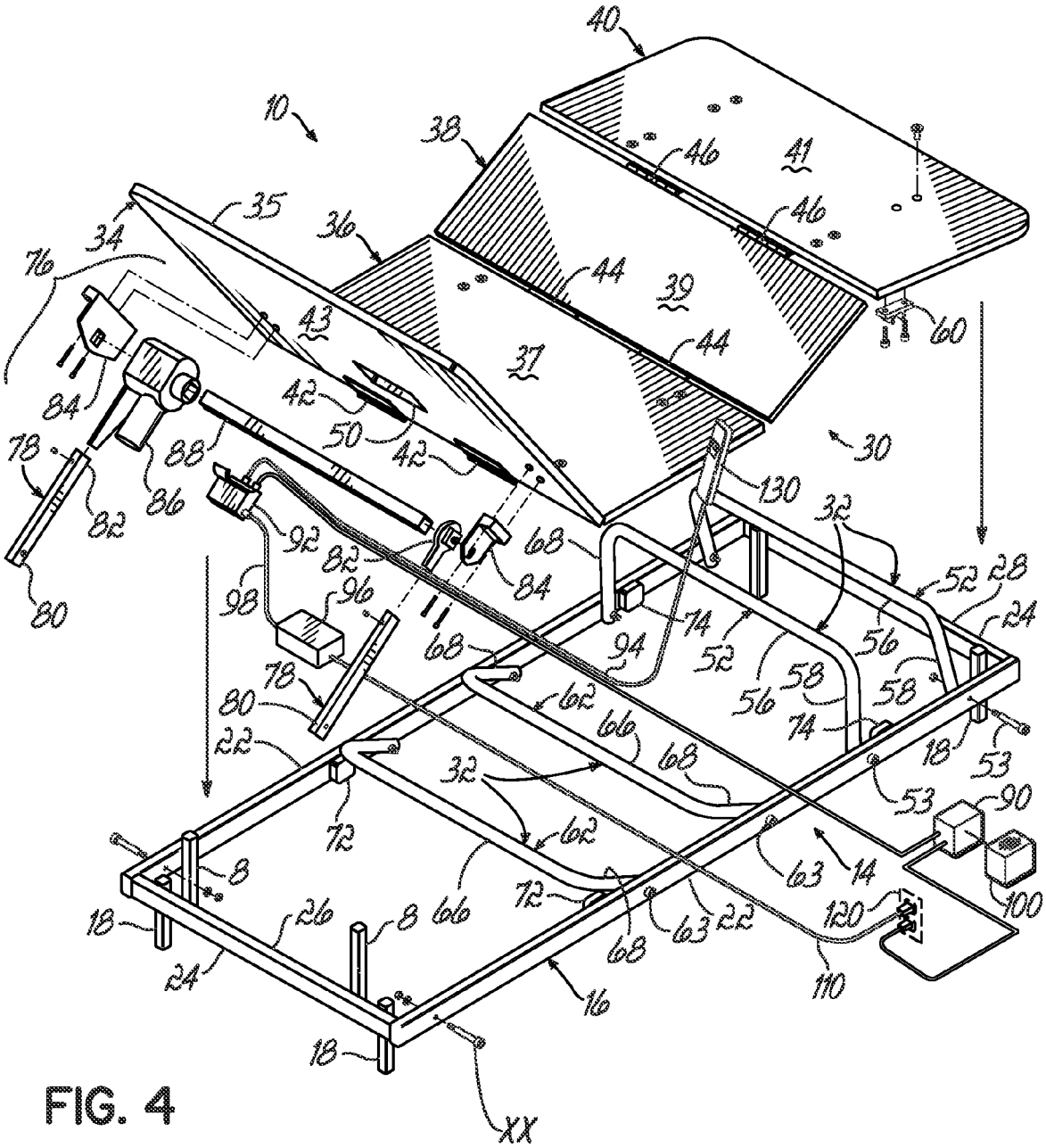
FIG. 4 is a disassembled exploded perspective view of the adjustable bed of FIG. 1 without the mattress.

The head deck board 34 is hingedly secured to the seat deck board 36 with hinges 42, in turn secured to the lower surfaces 43, 45 of the head and seat deck boards 34, 36, respectively. Similarly, seat deck board 36 is hingedly secured to leg deck board 38 with hinges 44, in turn secured to the lower surfaces 45, 47 of the seat and leg deck boards 36, 38, respectively. Leg deck board 38 is hingedly secured to foot deck board 40 with hinges 46, in turn secured to the lower surfaces 47, 49 of the leg and foot deck boards 38, 40, respectively. Although two hinges 42 are shown (FIGS. 1-4) securing the head deck board 34 to the seat deck board 36, any number of hinges may alternatively be used including one continuous hinge. The same applies to hinges 44 and 46 connecting the other deck boards. The deck boards 34, 36, 38 and 40 may be made of plywood, or may alternatively comprise plastic, oriented strand board or any other suitable material. As illustrated in FIGS. 1 and 4, the head deck board 34 may include a rectangular aperture 50 or an aperture of any suitable shape therein which may be used as a handle.

With continued reference to FIGS. 2-3, the adjustable bed 10 further comprises connectors 32 in the form of inverted U-shaped foot tubes 52. The adjustable bed 10 has two foot tubes 52 pivotally secured to the side rails 22 of the stationary frame 16 with fasteners 53 so that each pivots about a horizontal pivot axis 54. Each foot tube 52 has a center portion 56 and a pair of leg portions 58 extending downwardly from opposed ends of the center portion 56. The center portion 56 of each of the foot tubes 52 is secured to the foot deck board 40 with clips 60. Clips 60 are each secured to the lower surface 49 of the foot deck board 40. Although each foot tube 52 is illustrated being secured to two clips 60, any other methods and/or components for securing the foot tubes 52 to the foot deck board 40 may alternatively be used.

Two seat tubes or connectors 62 are pivotally secured to the side rails 22 of the stationary frame 16 with fasteners 63 so that each pivots about a horizontal pivot axis 64. Each seat tube 62 has a center portion 66 and a pair of leg portions 68 extending downwardly from opposed ends of the center portion 66. The center portion 66 of each of the foot tubes 62 is secured to the seat deck board 36 with clips 70. Clips 70 are secured to the lower surface 45 of the seat deck board 36. Although each seat tube 62 is illustrated being secured to two clips 70, any other methods and/or components for securing the seat tubes 62 to the seat deck board 36 may alternatively be used.

With reference to FIGS. 2-4, two stops 72 are each secured to the inside surfaces of the side rails 22 of the frame 16 to prevent the seat tubes 62 from moving too far forwardly i.e. towards the head end of the bed. Similarly, two stops 74 are each secured to the inside surfaces of the side rails 22 of the frame 16 to prevent the foot tubes 52 from moving too far rearward i.e. towards the foot end of the bed. The articulated deck 30 may be moved by a motorized drive assembly 76 between a fully horizontal position (FIG. 2) in which the deck boards 34, 36, 38 and 40 are generally co-planar in a horizontal position or orientation and a fully inclined position (FIG. 3). In the fully inclined position, the head deck board 34 is inclined, the seat deck board 36 is substantially horizontal, the leg deck board 36 inclined and the foot deck board 40 slightly inclined. When the articulated deck 30 is in its fully horizontal position (FIG. 2), two braces 8, each secured to the head rail 26 of the frame 18 and extending upwardly therefrom, support the head deck board 34 of the articulated deck 30.

With reference to FIG. 4, the motorized drive assembly 76 (shown disassembled) may comprise two lever arms 78 pivotally secured at their respective lower ends 80 to the side rails 22 of the frame 16 such that each of the lever arms 78 pivots about a horizontal pivot axis 79. The lever arms 78 may have a fixed length. The upper ends 82 of the lever arms 78 are secured to brackets 84 which are, in turn, secured to the lower surface 43 of the head deck board 34. An electric motor 86 is secured to one of the lever arms 78. Alternatively, the electric motor 86 may be secured to the head deck board 34 or to any other suitable location or surface. The electric motor 86 [maybe] *may be* one of any suitable type, such as one manufactured by German manufacturer Hettich-Franke GmbH under the model designation Mosys Classic 1.61.03.

The output of the electric motor 86 drives or rotates a drive tube 88 that extends between the upper ends 82 of the lever arms 78. The electric motor 86 may be powered by a power supply 96 and may be controlled via a sensor assembly including, for example, a microphone 100 coupled to a processor 90. The power supply 96, microphone 100 and the processor 90 may be electrically powered, via respective connections, to a power source such as one in the form of a wall outlet 120. The electric motor 86 may be further controlled via a remote unit 130 coupled to a control unit 92 with a line 94.

With continued reference to FIG. 4, microphone 100 is suitably selected and configured to detect and distinguish sounds such as those produced by conventional human snoring. Microphone 100 may be positioned proximate adjustable bed 10 or at any other suitable location such that it may detect sounds made by a person (not shown) lying on the mattress 12 (FIG. 1). Processor 90 is suitably connected to microphone 100 such that processor 90 may receive a signal from microphone 100 and send, when a specific set of logic conditions is met, a signal or set of signals, such as an electric signal, to the electric motor 86. Such signal may be sent directly to the electric motor 86 or may alternatively be sent via control unit 92, as depicted in FIG. 4.

With reference to FIGS. 2-3, in operation starting from the fully horizontal position of the adjustable bed 10 shown in FIG. 2 in which the articulated deck 30 is generally horizontal, the microphone 100 or similar device detects a sound corresponding to snoring coming from a person sleeping on the adjustable bed 10. The signal is processed by the processor 90, which recognizes the sound and sends a signal to the electric motor 86, as described above, thereby actuating the motor 86. Activation of the motor 86 rotates the drive tube 88 which causes the lever arms 78 of the drive assembly 76 to rotate or pivot about horizontal axis 79 at the lower ends 80 of the lever arms 78 i.e. where the lever arms 78 are pivotally secured to the side rails 22 of the frame 18. Thus, the head deck board 34 moves from its fully horizontal position (FIG. 2) to a second position (not shown) between the first horizontal position and the fully inclined position (FIG. 3) in which the head edge 102 of the head deck board 34 is above the rear edge 104 of the head deck board 34. The transition from the fully horizontal position to the second position may induce the snoring person to change sleeping positions, thereby causing the snoring to stop.

The processor 90 may be configured to cause actuation of the electric motor 86 in one direction so as to cause the change in position described above from the fully horizontal position (FIG. 2) to a position between the fully horizontal position (FIG. 2) and the fully inclined position (FIG. 3). The processor 90 may be further configured such that, upon detection of a sound corresponding to human snoring, it will first detect the position of the head deck board 34 such that, if for example the head deck board 34 is in the second position, it will actuate the motor 86 to cause movement of the head deck board 34 from the second position to the fully horizontal position (FIG. 2) or to the fully inclined position (FIG. 3). Similarly, the processor 90 may be configured such that, upon detection of a sound corresponding to human snoring, it will first detect the position of the head deck board 34 and cause it to move from such position to any other position between the fully horizontal position (FIG. 2) and the fully inclined position (FIG. 3).

With continued reference to FIGS. [23] *2-3*, the processor 90 may be also configured such that after a predetermined length of time without detected snoring, it causes the head deck board 34 to return from any starting position between the fully horizontal position (FIG. 2) and the fully inclined position (FIG. 3) back to the fully horizontal position (FIG. 2). Processor 90 may also be configured or "taught", via components and methods known in the art, to recognize the snoring sound associated with a particular person, such that it will cause actuation of the electric motor 86 only when snoring from such particular person is detected.

Movement of the head deck board 34 between the fully horizontal position (FIG. 2) and the fully inclined position (FIG. 3) may be also achieved via manual actuation of the remote unit 130. Remote unit 130 may be further configured such that it can cause movement of the head deck board 34 between any starting position and any desired ending position between and including the fully horizontal position (FIG. 2) and the fully inclined position (FIG. 3). A user of the adjustable bed 10 may, therefore, be able, for example, to move the bed 10 from any starting position to the fully inclined position (FIG. 3). In such exemplary motion, as the head deck board 34 inclines, the person using the bed 10 may lean forward causing the rear edge 104 of the head deck board 34 to move towards the head end of the bed, causing or pulling the seat deck board 36 horizontally towards the head end of the bed. The seat deck board 36 also lowers due to the connectors 32 and more particularly, the seat tubes 62 pivoting about horizontal pivot axes 64 in a counterclockwise direction as shown in FIGS. 2-3.

With continued reference to FIGS. 2-3, as the seat deck board 36 moves downwardly and towards the head end of the bed, the leg deck board 38 moves or is pulled from its fully horizontal position (FIG. 2) to its fully inclined position (FIG. 3). In this fully inclined position, the front edge 106 of the leg deck board 38 is lower than the rear edge 108 of the leg deck board 38. This movement of the leg deck board 38 causes or pulls the foot deck board 40 towards the head end of the bed as the connectors 32 and in particular the foot tubes 52 are pivoted about horizontal pivot axes 54 in a counterclockwise direction. In its fully inclined position (FIG. 3), the front edge 110 of the foot deck board 40 is higher than the rear edge 112 of the foot deck board 40.

The adjustable bed 10 may be also moved from its fully inclined position (FIG. 3), in which the front edge 102 of the head deck board 34 is above the rear edge 104 of the head deck board 34, back to its fully horizontal position (FIG. 2) via use of the motorized drive assembly 76 along with the person using the bed 10 shifting his or her weight backwardly.

Accordingly, many further embodiments, applications and modifications of the invention will become readily apparent to those of ordinary skill in the art without departing from the scope of the invention which is intended to be defined by the claims appended hereto.

What is claimed is:

~~1. An adjustable bed comprising:~~

~~a stationary frame;~~

~~a first head deck mattress support member supported by said frame;~~

~~a second seat deck mattress support member supported by said frame and pivotally coupled to said first mattress support member;~~

~~a sensor assembly adapted to detect a sound associated with human snoring; and~~

~~a motorized drive assembly operatively coupled to said sensor assembly and to said first mattress support member;~~

~~wherein detection of said snoring sound actuates said motorized drive assembly thereby causing relative movement of said first mattress support member with respect to said second mattress support member along a transverse axis of the adjustable bed, between a horizontal flat position and an inclined position.~~

~~2. The adjustable bed of claim 1 wherein said sensor assembly is further adapted to recognize a sound associated with snoring of a particular person.~~

~~3. The adjustable bed of claim 1 wherein said motorized drive assembly is secured to said frame.~~

~~4. The adjustable bed of claim 1 wherein said motorized assembly comprises an electric motor.~~

~~5. The adjustable bed of claim 1 wherein:~~

~~said first mattress support member comprises a first edge;~~

~~said second mattress support member comprises a second edge generally parallel to and adjacent said first edge; and~~

~~said first and second mattress support members are pivotally coupled along said first edge.~~

~~6. The adjustable bed of claim 1 wherein said relative movement comprises incremental relative movements of said first mattress support member with respect to said second mattress support member.~~

~~7. The adjustable bed of claim 1 further comprising a leg deck mattress support member pivotally coupled to said second seat deck mattress support member.~~

~~8. The adjustable bed of claim 7 further comprising a foot deck mattress support member pivotally coupled to said leg deck mattress support member.~~

~~9. The adjustable bed of claim 8 further comprising a remote control unit configured to control relative movement of said first head deck mattress support member with respect to said second mattress support member.~~

~~10. The adjustable bed of claim 8 wherein said seat deck mattress support member, said leg deck mattress support member and said foot deck mattress support member each move toward said head deck mattress support member when said head deck mattress support member is inclined.~~

~~11. The adjustable bed of claim 1 wherein said motorized drive assembly comprises a processor operative to receive a signal from said sensor and when a specific set of logic conditions are met, send a signal to said motorized drive assembly, thereby to cause relative movement of said first mattress support member.~~

~~12. An adjustable bed comprising:~~

~~a stationary frame;~~

~~a first head deck mattress support member supported by said frame;~~

~~at least one other mattress support member supported by said frame, said at least one other mattress support member being pivotally coupled to said first mattress support member;~~

~~a sensor assembly adapted to detect a sound associated with human snoring; and~~

~~a motorized drive assembly operatively coupled to said sensor assembly and to said first mattress support member;~~

~~wherein detection of said snoring sound actuates said motorized drive assembly thereby causing relative movement of said first mattress support member with respect to said at least one other mattress support member along a transverse axis of the adjustable bed, between a horizontal flat position and an inclined position.~~

~~13. The adjustable bed of claim 12 wherein said motorized drive assembly comprises a processor operative to receive a signal from said sensor and when a specific set of logic conditions are met, send a signal to said motorized drive assembly, thereby to cause relative movement of said first mattress support member.~~

~~14. The adjustable bed of claim 12 wherein said sensor assembly is further adapted to recognize a sound associated with snoring of a particular person.~~

~~15. The adjustable bed of claim 12 wherein said motor assembly is secured to said frame.~~

~~16. The adjustable bed of claim 12 wherein said motorized assembly comprises an electric motor.~~

~~17. The adjustable bed of claim 12 wherein:~~

~~said first mattress support member comprises a first edge;~~

~~one of said at least one other support mattress member comprises a second edge generally parallel to and adjacent said first edge; and~~

~~said first mattress support member and said one of said at least one other mattress support member are pivotally coupled along said first edge.~~

~~18. The adjustable bed of claim 12 wherein said relative movement comprises incremental relative movements of said first mattress support member with respect to said at least one other mattress support member.~~

~~19. The adjustable bed of claim 12 further comprising a remote control unit configured to control relative movement of said first head deck mattress support member with respect to said at least one other mattress support member.~~

~~20. The adjustable bed of claim 12 wherein the detection by said sensor assembly of the cessation of said snoring sound for a predetermined length of time activates said motorized drive assembly to cause said first mattress support member to be moved back from an inclined position to a horizontal flat position.~~

*21. An adjustable bed comprising:*

*a stationary frame having a pair of opposed side rails, a head end rail and a foot end rail;*

*a pair of generally inverted U-shaped foot tubes pivotally secured to said side rails of said frame;*

*a pair of generally inverted U-shaped seat tubes pivotally secured to said side rails of said frame;*

*a head deck board;*

*a seat deck board secured to said seat tubes and hingedly secured to said head deck board;*

*a leg deck board hingedly secured to said seat deck board;*

*a foot deck board hingedly secured to said leg deck board and secured to said foot tubes;*

*a sensor assembly adapted to detect a sound associated with human snoring; and*

*a motorized drive assembly operatively coupled to said sensor assembly and comprising a pair of lever arms pivotally secured to said side rails of said frame and a motor secured to one of the lever arms for rotating a drive tube extending between the lever arms, said lever arms being operatively coupled to said head deck board, wherein activation of said motorized drive assembly causes movement of at least one of said deck boards,*

*wherein detection of said snoring sound actuates said motorized drive assembly thereby causing relative movement of said head deck board with respect to said seat deck board along a transverse axis of the adjustable bed, between a horizontal flat position and an inclined position.*

*22. The adjustable bed of claim 21 wherein said sensor assembly is further adapted to recognize a sound associated with snoring of a particular person.*

*23. The adjustable bed of claim 21 wherein said relative movement comprises incremental relative movements of said head deck board with respect to said seat deck board.*

*24. The adjustable bed of claim 21 further comprising a remote control unit configured to control relative movement of said head deck board with respect to said seat deck board.*

*25. The adjustable bed of claim 21 wherein said motorized drive assembly comprises a processor operative to receive a signal from said sensor assembly and when a specific set of logic conditions is met, send a signal to said motorized drive assembly, thereby to cause relative movement of said head deck board.*

*26. The adjustable bed of claim 21 wherein the detection by said sensor assembly of cessation of said snoring sound for a predetermined length of time activates said motorized drive assembly to cause said head deck board to be moved back from the inclined position to the horizontal flat position.*

*27. The adjustable bed of claim 21 wherein said seat deck board moves towards said head end rail and lowers when said head deck board is inclined.*

*28. The adjustable bed of claim 21 wherein said seat deck board, said leg deck board and said foot deck board each moves toward said head end rail when said head deck board is inclined.*

*29. An adjustable bed comprising:*

*a stationary frame having a pair of opposed side rails, a head end rail and a foot end rail;*

*a pair of generally inverted U-shaped seat tubes pivotally secured to said side rails of said frame;*

*a head deck board;*

*a seat deck board secured to said seat tubes and hingedly secured to said head deck board;*

*a sensor assembly adapted to detect a sound associated with human snoring; and*

*a motorized drive assembly operatively coupled to said sensor assembly and comprising a pair of lever arms pivotally secured to said side rails of said frame and a motor secured to one of the lever arms for rotating a drive tube extending between the lever arms, said lever arms being operatively coupled to said head deck board, wherein activation of said motorized drive assembly causes movement of at least one of said deck boards,*

*wherein detection of said snoring sound actuates said motorized drive assembly thereby causing relative movement of said head deck board with respect to said seat deck board along a transverse axis of the adjustable bed, between a horizontal flat position and an inclined position.*

*30. The adjustable bed of claim 29 wherein said sensor assembly is further adapted to recognize a sound associated with snoring of a particular person.*

*31. The adjustable bed of claim 29 wherein said relative movement comprises incremental relative movements of said head deck board with respect to said seat deck board.*

*32. The adjustable bed of claim 29 further comprising a remote control unit configured to control relative movement of said head deck board with respect to said seat deck board.*

*33. The adjustable bed of claim 29 wherein said motorized drive assembly comprises a processor operative to receive a signal from said sensor assembly and when a specific set of logic conditions is met, send a signal to said motorized drive assembly, thereby to cause relative movement of said head deck board.*

*34. The adjustable bed of claim 29 wherein the detection by said sensor assembly of cessation of said snoring sound for a predetermined length of time activates said motorized drive assembly to cause said head deck board to be moved back from the inclined position to the horizontal flat position.*

*35. The adjustable bed of claim 29 wherein said seat deck board moves towards said head end rail and lowers when said head deck board is inclined.*

*36. An adjustable bed comprising:*

*a stationary frame;*

*a pair of generally inverted U-shaped foot tubes pivotally secured to said frame;*

*a pair of generally inverted U-shaped seat tubes pivotally secured to said frame;*

*a seat deck board secured to said seat tubes;*

*a foot deck board secured to said foot tubes, a leg deck board hingedly secured to and positioned between said seat deck board and said foot deck board;*

*a head deck board hingedly secured to said seat deck board;*

*a sensor assembly adapted to detect a sound associated with human snoring; and*

*a motorized drive assembly comprising a pair of lever arms pivotally secured to said frame and a motor for rotating a drive tube extending between the lever arms, said lever arms being operatively coupled to said head deck board, wherein activation of said motorized drive assembly causes said head deck board to move between an inclined position and a flat position,*

*wherein detection of said snoring sound actuates said motorized drive assembly thereby causing relative movement of said head deck board with respect to at least one other of said deck boards along a transverse axis of the adjustable bed, between a horizontal flat position and an inclined position.*

*37. The adjustable bed of claim 36 further comprising a remote control unit configured to control relative movement of said head deck board with respect to said seat deck board.*

*38. The adjustable bed of claim 36 wherein said seat deck board, said leg deck board and said foot deck board each moves when said head deck board is inclined.*

*39. The adjustable bed of claim 36 wherein said sensor assembly is further adapted to recognize a sound associated with snoring of a particular person.*

*40. The adjustable bed of claim 36 wherein said motorized drive assembly comprises a processor operative to receive a signal from said sensor assembly and when a specific set of logic conditions is met, send a signal to said motorized drive assembly, thereby to cause relative movement of said head deck board.*

* * * * *